(12) United States Patent
McLaughlin et al.

(10) Patent No.: US 12,224,094 B2
(45) Date of Patent: Feb. 11, 2025

(54) MAGNETIC SIGNATURE IMPRINTING SYSTEM

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 213 days.

(21) Appl. No.: 17/955,120

(22) Filed: Sep. 28, 2022

(65) Prior Publication Data
US 2023/0096231 A1     Mar. 30, 2023

Related U.S. Application Data

(60) Provisional application No. 63/250,057, filed on Sep. 29, 2021.

(51) Int. Cl.
*H01F 13/00*      (2006.01)
*A61B 90/00*      (2016.01)

(52) U.S. Cl.
CPC ............ *H01F 13/00* (2013.01); *A61B 90/39* (2016.02); *A61B 2090/3954* (2016.02)

(58) Field of Classification Search
CPC .. H01F 13/00; A61B 90/39; A61B 2090/3954
See application file for complete search history.

(56) References Cited

U.S. PATENT DOCUMENTS

| | | | |
|---|---|---|---|
| 4,940,966 | A | 7/1990 | Pettigrew et al. |
| 10,188,310 | B2 | 1/2019 | Derichs et al. |
| 11,281,869 | B2 | 3/2022 | Vartiovaara |
| 2003/0094487 | A1 | 5/2003 | Blankenship et al. |
| 2008/0041248 | A1 | 2/2008 | Kuwabara et al. |
| 2009/0012418 | A1 | 1/2009 | Gerlach |

(Continued)

FOREIGN PATENT DOCUMENTS

| | | |
|---|---|---|
| EP | 2997901 A1 | 3/2016 |
| WO | 2013034175 A1 | 3/2013 |

(Continued)

OTHER PUBLICATIONS

PCT/US2022/044234 filed Sep. 21, 2022 International Preliminary Report on Patentability dated Apr. 2, 2024.

(Continued)

*Primary Examiner* — Chao Sheng
(74) *Attorney, Agent, or Firm* — Rutan & Tucker LLP

(57) ABSTRACT

Disclosed herein is a magnetic signature imprinting system including an imprinting device and a medical device including ferrous elements. The imprinting device includes an active area having a magnet moving system, one or more sensors, and a console. The magnet moving system is configured to change the location or orientation of one or more magnets to generate one or more magnetic fields to imprint a magnetic signature. The one or more sensors are configured to detect one or more characteristics of the medical device and the console is in communication with the magnet moving system and the one or more sensors.

29 Claims, 8 Drawing Sheets

(56) References Cited

U.S. PATENT DOCUMENTS

| | | |
|---|---|---|
| 2013/0029112 A1 | 1/2013 | Bargir et al. |
| 2014/0253270 A1* | 9/2014 | Nicholls ................ A61B 5/062 335/284 |
| 2014/0290512 A1 | 10/2014 | Raksha |
| 2015/0178522 A1 | 6/2015 | Cato et al. |
| 2016/0008091 A1 | 1/2016 | Saotome et al. |
| 2016/0262844 A1 | 9/2016 | Cohen et al. |
| 2017/0238996 A1 | 8/2017 | Frame et al. |
| 2018/0117419 A1 | 5/2018 | Jackson |
| 2018/0221610 A1 | 8/2018 | Larson et al. |
| 2018/0310955 A1 | 11/2018 | Lindekugel et al. |
| 2020/0250385 A1 | 8/2020 | Narayanan et al. |
| 2020/0298493 A1 | 9/2020 | Wilds et al. |
| 2020/0360662 A1* | 11/2020 | Ma ....................... H01F 13/003 |
| 2020/0405406 A1 | 12/2020 | Harris et al. |
| 2021/0113113 A1 | 4/2021 | Weprin et al. |
| 2021/0174378 A1 | 6/2021 | Rahimizad et al. |
| 2023/0101371 A1 | 3/2023 | Sowards et al. |
| 2023/0102059 A1 | 3/2023 | Sowards et al. |
| 2023/0285096 A1 | 9/2023 | Lambrecht et al. |
| 2023/0334502 A1 | 10/2023 | Top et al. |

FOREIGN PATENT DOCUMENTS

| | | |
|---|---|---|
| WO | 2023055628 A1 | 4/2023 |
| WO | 2023055821 A1 | 4/2023 |
| WO | 2023055958 A1 | 4/2023 |

OTHER PUBLICATIONS

U.S. Appl. No. 17/949,679, filed Sep. 21, 2022 Non-Final Office Action dated May 22, 2024.

PCT/US2022/044234 filed Sep. 21, 2022 International Search Report and Written Opinion dated Dec. 16, 2022.

PCT/US2022/045264 filed Sep. 29, 2022 International Search Report and Written Opinion dated Jan. 27, 2023.

PCT/US2022/045069 filed Sep. 28, 2022 International Search Report and Written Opinion dated Mar. 14, 2023.

U.S. Appl. No. 17/949,679, filed Sep. 21, 2022 Non-Final Office Action dated Oct. 25, 2024.

U.S. Appl. No. 17/956,651, filed Sep. 29, 2022 Non-Final Office Action dated Nov. 14, 2024.

* cited by examiner

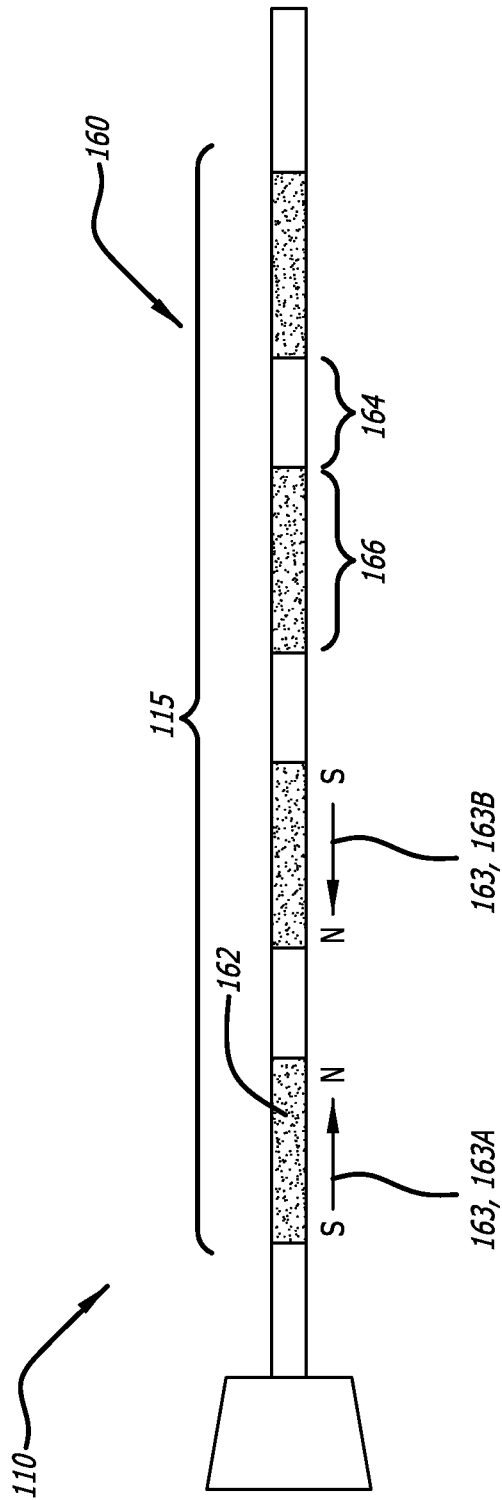

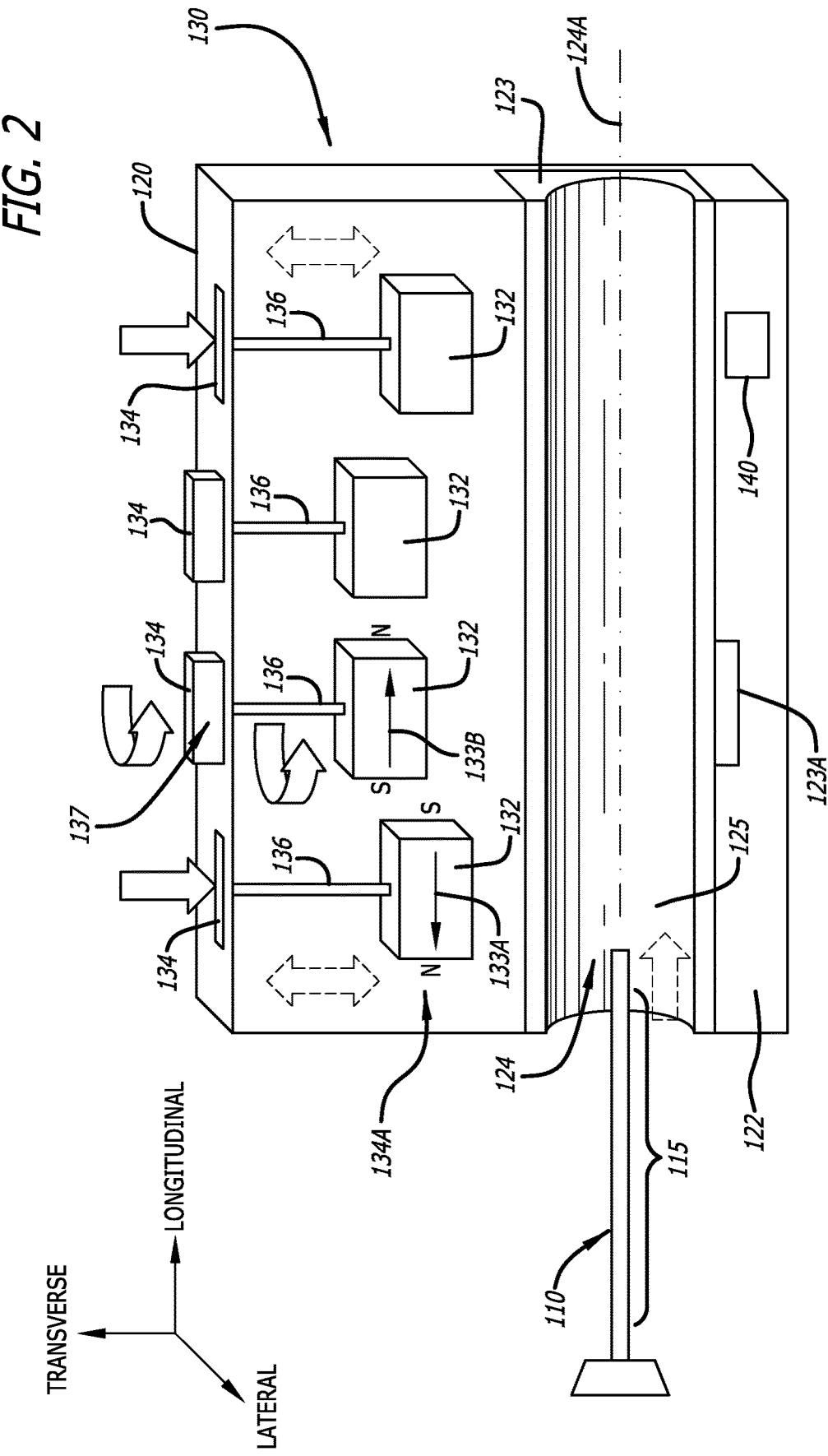

MAGNETIC SIGNATURE IMPRINTING SYSTEM

PRIORITY

This application claims the benefit of priority to U.S. Provisional Application No. 63/250,057, filed Sep. 29, 2021, which is incorporated by reference in its entirety into this application.

BACKGROUND

Many medical devices used in non-invasive and invasive procedures include ferrous elements. A magnetic signature may be imprinted onto the ferrous elements, allowing the medical device to be tracked in three-dimensional space. However, current methodologies are limited to a single imprinted configuration, limiting the number of distinct imprinted medical devices for simultaneous use. It would be beneficial to the user to have a system configured to imprint multiple magnetic signatures onto medical devices, allowing users to use and track distinct medical devices in three-dimensional space. Disclosed herein are a magnetic signature imprinting system and a method that addresses the foregoing.

SUMMARY

Disclosed herein is a magnetic signature imprinting system that, according to some embodiments, includes an imprinting apparatus configured to operatively engage a medical device, where the imprinting apparatus includes a frame and a device engagement member coupled with the frame. The device engagement member is configured to receive and position a signature portion of the medical device within an imprinting space of the frame. The apparatus further includes a number of magnets that selectively positionable with respect to the imprinting space via one or more magnet actuators coupled between the number of magnets and the frame. The system further includes a console coupled with the one or more magnet actuators, the console having a number of processors and a non-transitory computer-readable medium having logic stored thereon that, when executed by the processors, perform operations that include activating the one or more magnet actuators to (i) displace the magnets into an imprinting position defining a magnetic field within the imprinting space, where the magnetic field is configured to imprint a defined magnetic signature on the signature portion and (ii) displace the magnets away from the imprinting position. In some embodiments, the medical device includes a needle, a stylet, a guidewire, an obturator, a probe, or a tunneller.

In some embodiments, the magnetic signature includes a series of dipoles disposed along the signature portion. In some embodiments, at least one dipole includes a first length and at least one other dipole includes a second length different from the first length. In some embodiments, at least one dipole includes a first orientation and at least one other dipole includes a second orientation rotated 180 degrees from the first orientation. In some embodiments, a first spacing between a first pair of adjacent dipoles is different from a second spacing between a second pair of adjacent dipoles. In some embodiments, the magnetic signature includes one or more multipoles disposed along the signature portion and in some embodiments, one or more of the number of magnets include multipoles.

In some embodiments, the system further includes a number of identification sensors coupled with the console, where the number of identification sensors are configured to provide at least one of data or electrical signals associated with one or more characteristics of the medical device, and where the operations further include (i) receiving the at least one of data or electrical signals from the number of identification sensors, (ii) determining an identity of the medical device based on the at least one of data or electrical signals, and (iii) establishing the defined magnetic signature based on the identity. In some embodiments, the number of identification sensors includes an RFID reader, and the operations include receiving RFID data from an RFID tag associated with the medical device, where the RFID data includes the identity. In some embodiments, the number of identification sensors includes a barcode reader, and the operations further include obtaining barcode data from a barcode associated with the medical device, where the barcode data includes the identity. In some embodiments, the number of identification sensors include one or more identification sensors configured to provide the at least one of data or electrical signals based on a number of physical characteristics of the medical device, and the operations further include determining the identity based on the number of physical characteristics. In some embodiments, the number of physical characteristics include one or more a physical dimension or a shape of the medical device. In some embodiments, the physical dimension includes a length or a diameter of a cannula.

In some embodiments, the one or more identification sensors include at least one of an inductive sensor, an impedance sensor, a capacitive sensor, or an optical sensor.

In some embodiments, the device engagement member includes a trough configured to receive the signature portion of the medical device therein.

In some embodiments, the number of magnets include passive magnets.

In some embodiments, the system further includes a number of magnetometers coupled with the console, where the magnetometers are configured to detect a magnetic field generated by a magnetic signature imprinted on the medial device, and the operations further include (i) receiving electrical signals from the magnetometers based on the magnetic field generated by a magnetic signature imprinted on the medial device, (ii) determining an imprinted magnetic signature on the medical device from the electrical signals from the magnetometers, (iii) comparing the imprinted magnetic signature on the medical device with the defined magnetic signature to verify that the imprinted magnetic signature matches the defined magnetic signature, and (iv) providing an alert to the operator in response to the comparison.

In some embodiments, activating the one or more magnet actuators includes selectively (i) displacing at least a first subset of the number of magnets into the imprinting position and (ii) extracting the at least a first subset of the number of magnets away from the imprinting position, the at least a first subset chosen from the number of magnets based on the defined magnetic signature.

In some embodiments, at least a second subset of the number of magnets is rotatable between a first magnet orientation and a second magnet orientation that is rotated 180 degrees with respect to the first magnet orientation.

In some embodiments, the imprinting apparatus includes one or more orienting actuators coupled between the at least a second subset of the number of magnets and the frame, and the operations further include activating the one or more orienting actuators to selectively rotate one or more of the at least a second subset of the number of magnets between the first magnet orientation and the second magnet orientation based on the defined magnetic signature.

In some embodiments, the number of magnets includes at least a third subset having a third magnet length and at least a fourth subset having a fourth magnet length that is different from the third magnet length.

In some embodiments, at least a fifth subset of the number of magnets includes magnets arranged in linear array extending along a longitudinal axis of the imprinting space, where each of the at least a fifth subset of the number of magnets is coupled to the frame via a linear magnet actuator, and where activating the one or more magnet actuators includes activating one or more of the linear magnet actuators to linearly displace one or more of the fifth subset of the number of magnets laterally toward the longitudinal axis of the imprinting space based on the defined magnetic signature.

In some embodiments, at least a sixth subset of the number of magnets includes magnets arranged along a turntable, where the turntable is rotatable about a turntable axis that is oriented perpendicular to the longitudinal axis of the imprinting space so that rotating the turntable selectively displaces the each of magnets of the sixth subset into and away from the imprinting position. The turntable is coupled with the frame via a turntable actuator, and activating the one or more magnet actuators includes activating the turntable actuator based on the defined magnetic signature.

In some embodiments, at least a seventh subset of the number of magnets includes magnets arranged along a circumference of a number of wheels, where each of the number of wheels is rotatable about a corresponding wheel axis that is oriented parallel to the longitudinal axis of the imprinting space so that rotating the number of wheels displaces each of the magnets of the seventh subset into and away from the imprinting position. Each wheel is coupled with the frame via a corresponding wheel actuator, and activating the one or more magnet actuators includes selectively activating at least one of the corresponding wheel actuators based on the defined magnetic signature.

In some embodiments, the magnets of the sixth and seventh subsets include dipoles having different lengths, orientation, and spacing.

In some embodiments, the device engagement member is coupled with the frame via an engagement member actuator configured to displace the engagement member along the longitudinal axis of the imprinting space, and the operations further include activating the engagement member actuator based on the defined magnetic signature to displace the engagement member between (i) a first engagement member position defining a first longitudinal position of the signature portion within the imprinting space and (ii) at least a second engagement member position defining a second longitudinal position of the signature portion within the imprinting space, where the first engagement member position is different from the at least a second engagement member position.

In some embodiments, the imprinting apparatus includes a number of position sensors configured to determine a longitudinal position of the signature portion within the imprinting space, and the operations further include at least one of (i) notifying the operator regarding the longitudinal position of the signature portion or (ii) activating the engagement member actuator to adjust the longitudinal position of the signature portion.

In some embodiments, the number of position sensors include one more magnetometers configured to determine a longitudinal position of at least a portion of the imprinted magnetic signature within the imprinting space, and the operations further include activating the engagement member actuator to adjust the longitudinal position of the at least a portion of the imprinted magnetic signature within the imprinting space.

Also disclosed herein is a method of imprinting a magnetic signature onto a medical device that, according to some embodiments, includes (i) receiving at least a signature portion of the medical device within an imprinting space of a magnetic signature imprinting system, (ii) determining an identity of the medical device, (iii) determining a defined magnetic signature to imprint onto the signature portion, (iv) imprinting a magnetic signature based on the defined magnetic signature onto the signature portion to define an imprinted magnetic signature, and (v) validating the imprinted magnetic signature.

In some embodiments of the method, the magnetic signature includes a series of dipoles disposed along the signature portion.

In some embodiments, the method further includes receiving at least one of data or electrical signals from the number of identification sensors of the system, where the at least one of data or electrical signals are based on a number of physical characteristics of the medical device, and where determining an identity of the medical device is based on as least one physical characteristics of the medical device.

In some embodiments of the method, validating the imprinted magnetic signature includes (i) determining the imprinted magnetic signature via a number of magnetometers of the system and (ii) comparing the imprinted magnetic signature with the defined magnetic signature to verify that the imprinted magnetic signature matches the defined magnetic signature.

In some embodiments of the method, imprinting a magnetic signature includes displacing at least a first subset of a number of magnets of the system into an imprinting position with respect to the signature portion, where the at least a first subset of a number of magnets is chosen based on the defined magnetic signature.

In some embodiments of the method, imprinting a magnetic signature includes activating one or more orienting actuators coupled with at least a second subset of the number of magnets to selectively rotate one or more of the at least a second subset of the number of magnets between a first magnet orientation and a second magnet orientation based on the defined magnetic signature.

In some embodiments of the method, the number of magnets includes at least a third subset having a third magnet length and at least a fourth subset having a fourth magnet length that is different from the third magnet length.

In some embodiments of the method, the number of magnets of the include dipoles having different dipole lengths, different dipole orientations, and different spacings between adjacent diploes.

In some embodiments of the method, the receiving at least a signature portion of the medical device includes coupling the medical device with an engagement member of the system, and the imprinting a magnetic signature includes displacing the engagement member based on the defined magnetic signature between (i) a first engagement member position defining a first longitudinal position of the signature portion within the imprinting space and (ii) at least a second engagement member position defining a second longitudinal position of the signature portion within the imprinting space, where the first engagement member position is different from the at least a second engagement member position.

In some embodiments of the method, imprinting a magnetic signature includes (i) determining a longitudinal position of at least a portion of the imprinted magnetic signature within the imprinting space via one or more magnetometers, and (ii) displacing the engagement member to adjust the longitudinal position of the at least a portion of the imprinted magnetic signature within the imprinting space.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1B illustrates a view of a medical device of the system of FIG. 1A, in accordance with some embodiments;

FIG. 2 illustrates a cross sectional illustration of the imprinting device of FIG. 1A, in accordance with some embodiments;

Figure 1A:
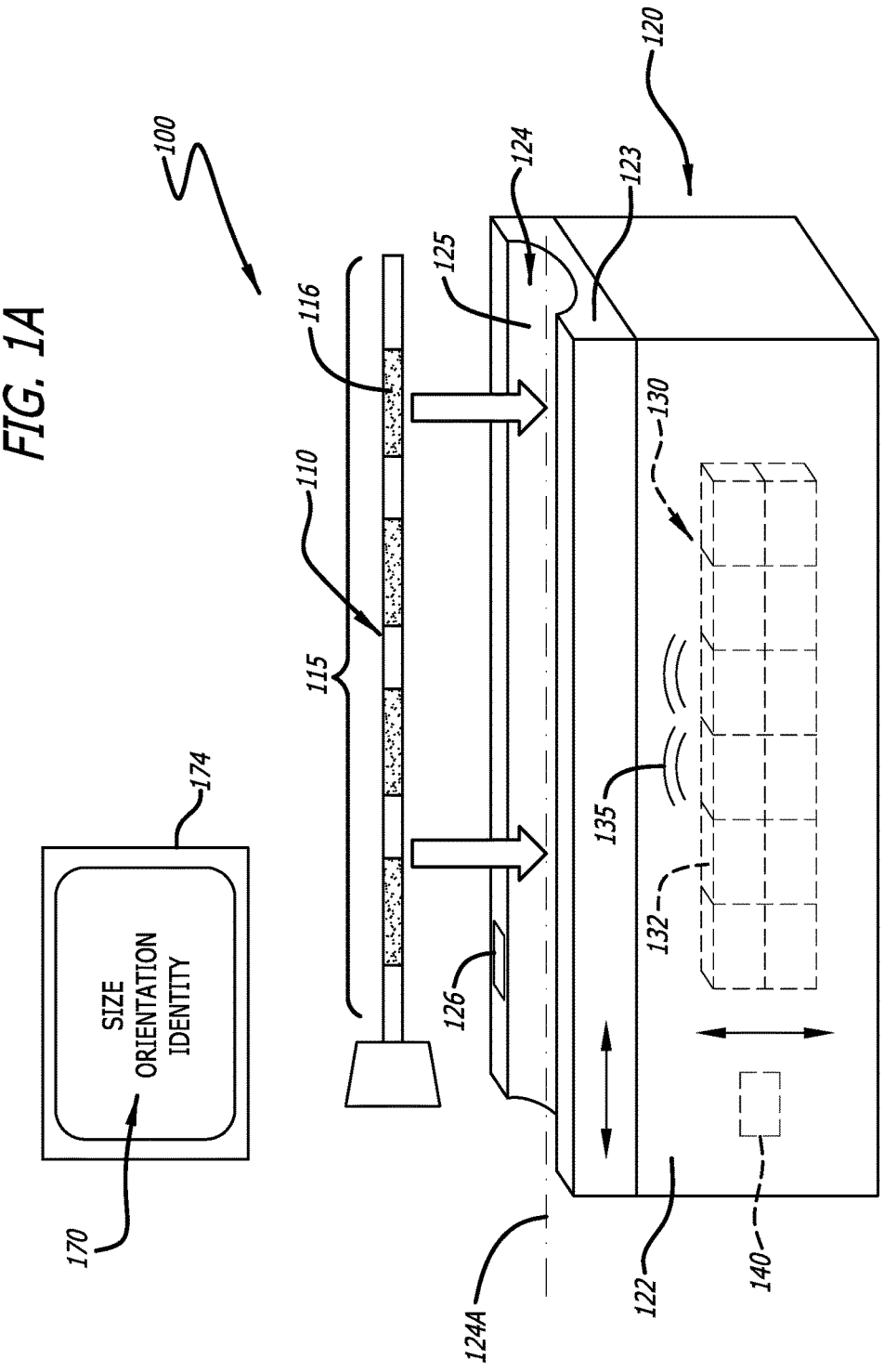
FIG. 1A illustrates a perspective view of a magnetic signature imprinting system, in accordance with some embodiments.
Figure 3:
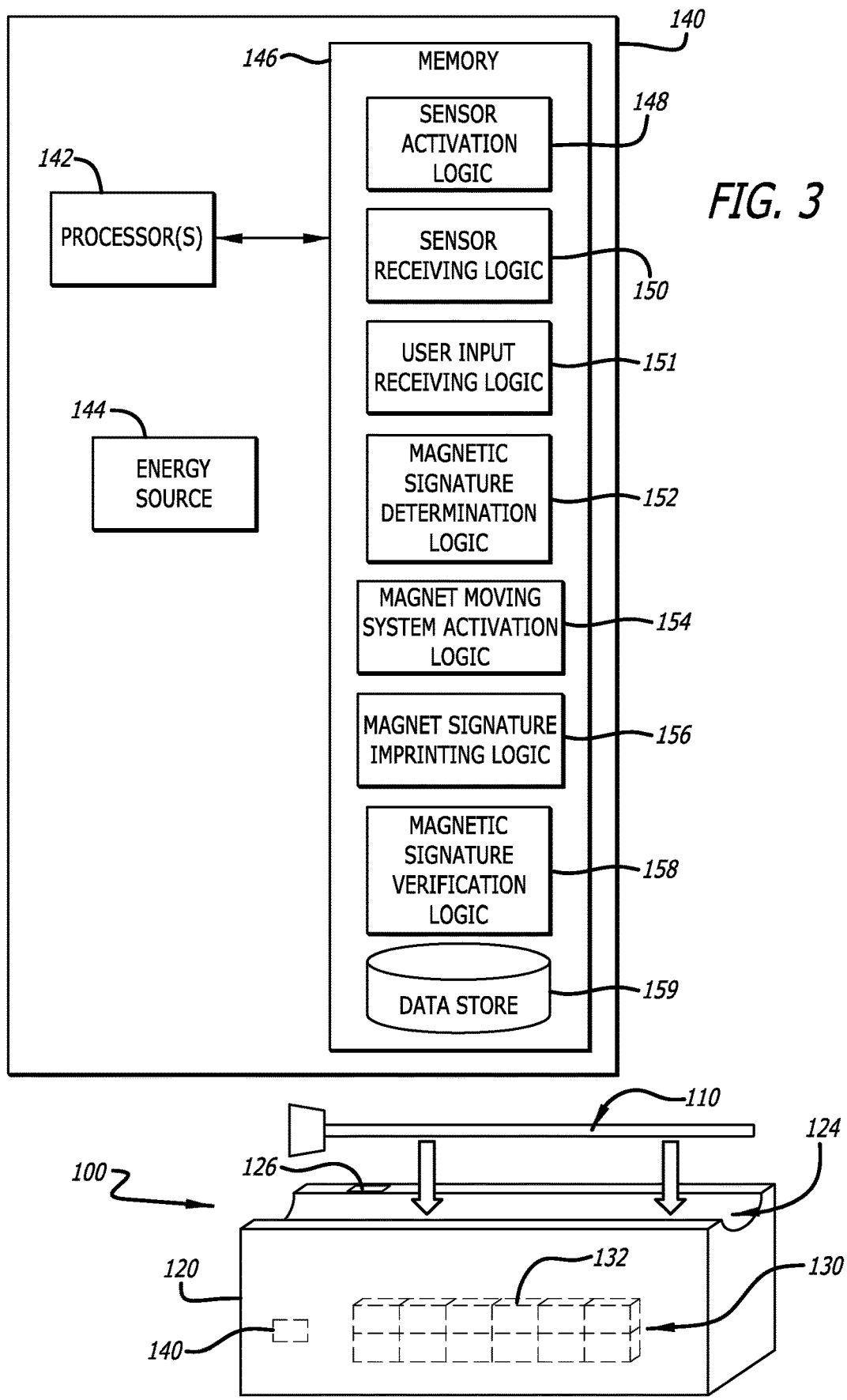
Figure 4:
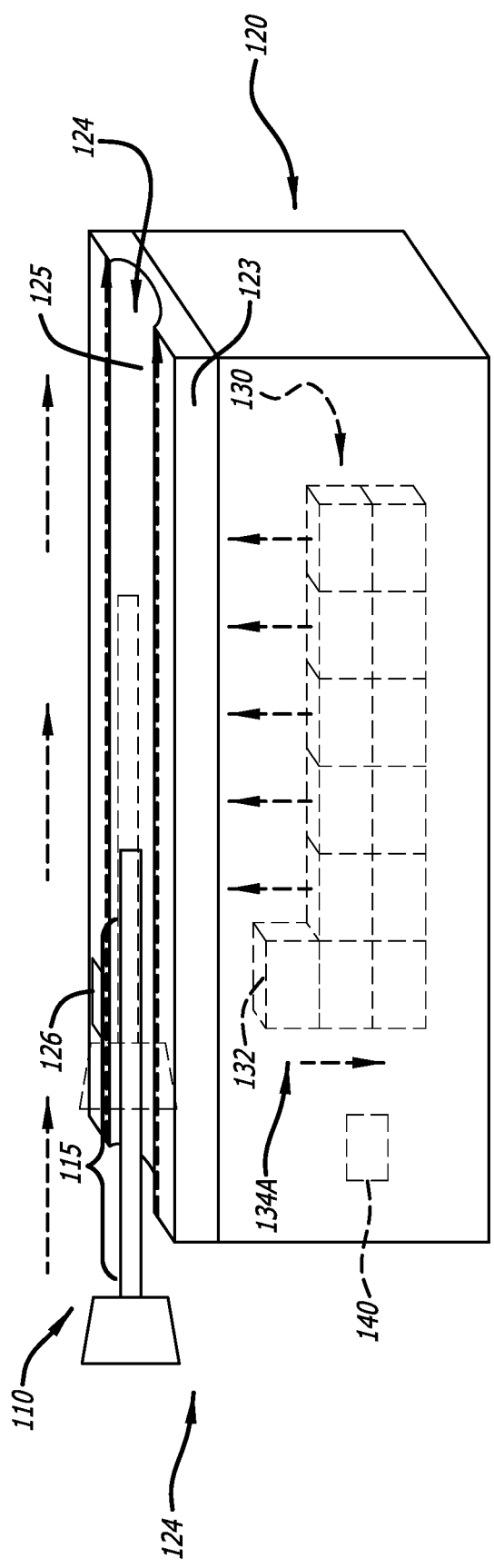
Figure 5:
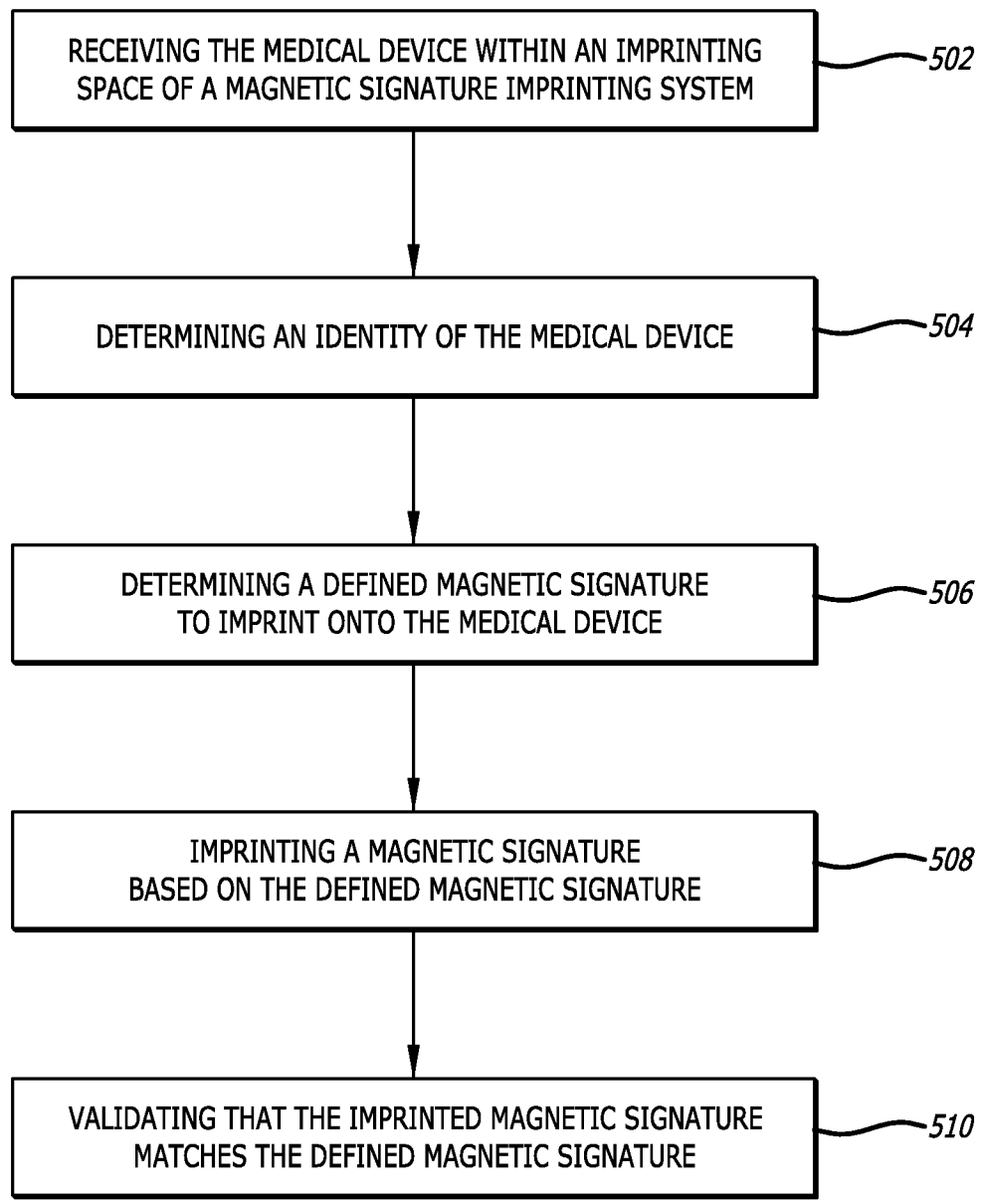
Figure 6:
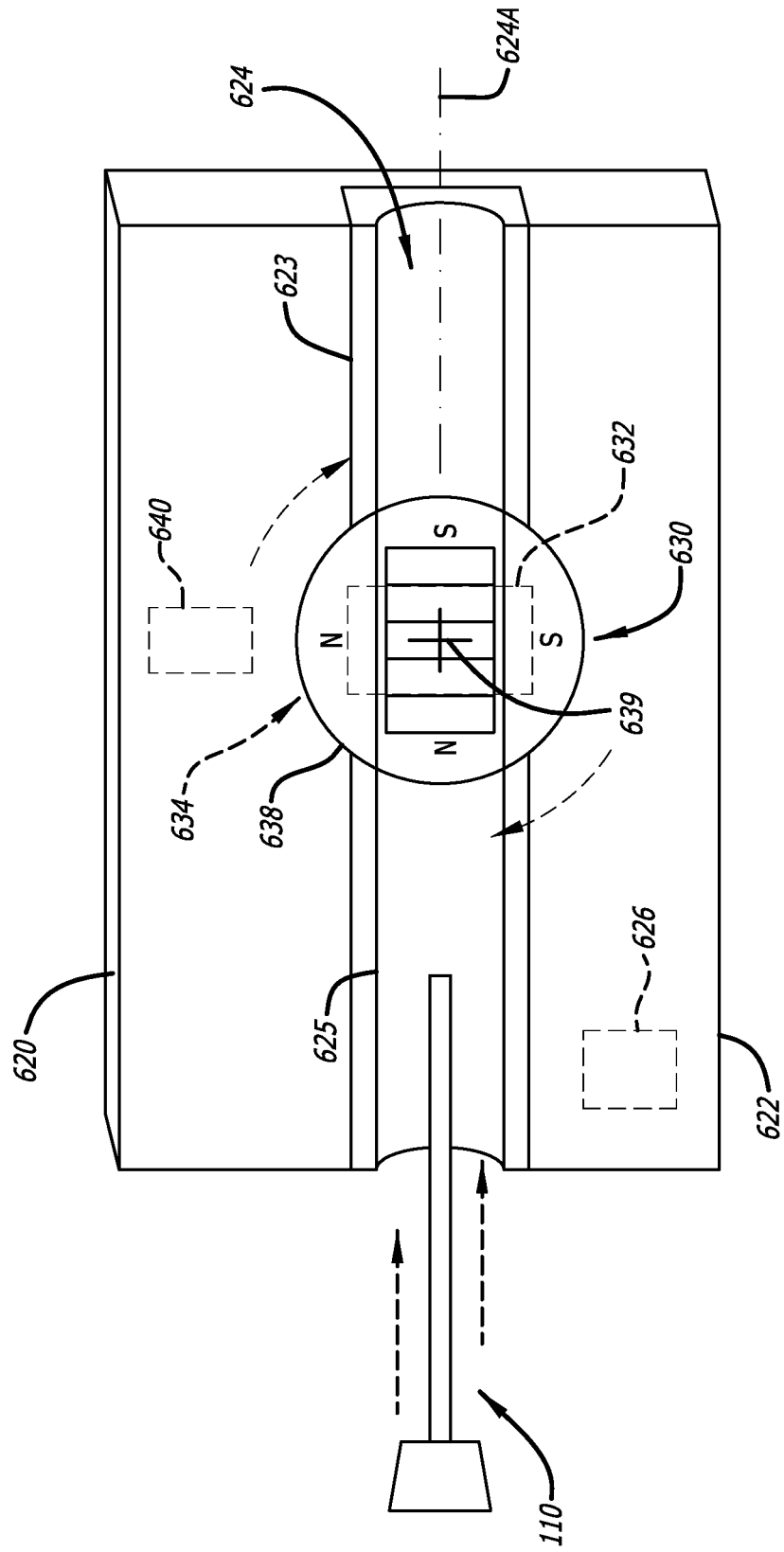
Figure 7:
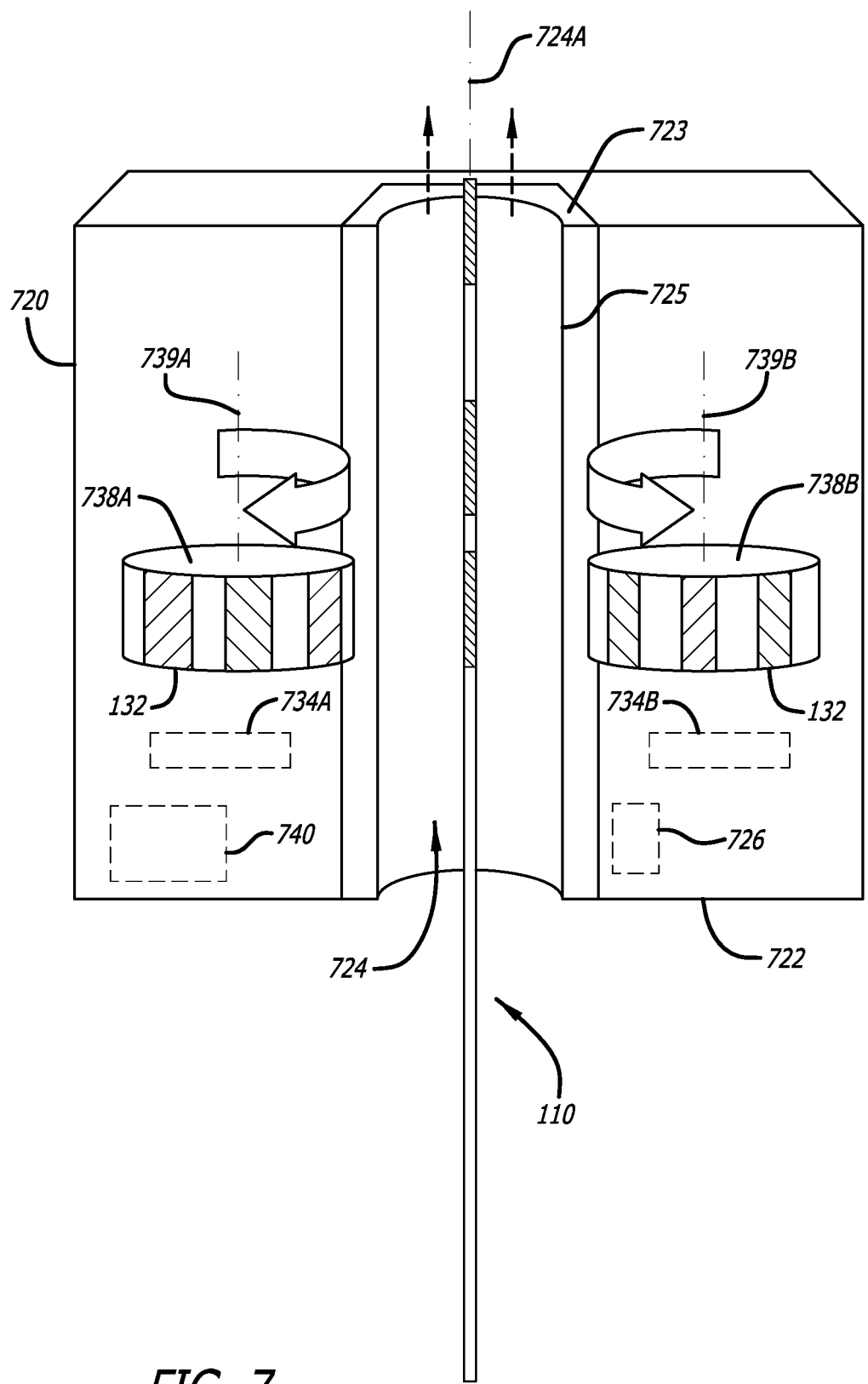

FIG. 3. illustrates a block diagram of some components of the system of FIG. 1A including a console, in accordance with some embodiments;

FIG. 4 is a perspective view of the imprinting device of the system of FIG. 1A illustrating an exemplary method of imprinting the magnetic signature onto the medical device, in accordance with some embodiments;

FIG. 5 illustrates a flow chart of an exemplary method of imprinting a magnetic signature onto a medical device, in accordance with some embodiments;

FIG. 6 is a top perspective view of a second embodiment of the imprinting device of FIG. 1A, in accordance with some embodiments; and FIG. 7 is a top perspective view of a third embodiment of the imprinting device of FIG. 1A, in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

FIG. 1A illustrates a perspective view of a magnetic signature imprinting system 100, in accordance with some embodiments. In some embodiments, the magnetic signature imprinting system ("system") 100 may include an imprinting device ("device") or apparatus 120 configured to receive therein or thereon, a medical device 110 having a signature portion 115, where the signature portion 115 may include ferrous elements (or portions) 116. The medical device 110 is exposed to one or more magnetic fields 135 of the imprinting device 120 to imprint a magnetic signature 160

(see FIG. 1B) onto the signature portion 115. The magnetic fields 135 are defined by the system 100 to imprint a magnetic signature 160 onto the signature portion 115, where the magnetic signature 160 may be distinct from any number of other magnetic signatures. Once imprinted on the medical device 110, the magnetic signature 160 may be detected (i.e., read or determined) by a medical device system. The magnetic signature 160 may also be tracked in three-dimensional space by a medical device tracking system. The system 110 may also include a console 140 including one or more processors and logic stored in memory (e.g., non-transitory computer-readable medium).

The device 120 may include a device body (or frame) 122 having an active area 124 (i.e., an imprinting space) configured to receive the medical device 110 therein or thereon. In some embodiments, the active area 124 may be the location where the medical device 110 is imprinted with the magnetic signature 160 by exposing the medical device 110 to the magnetic fields therein. In some embodiments, the signature portion 115 of the medical device 110 or the entire medical device 110 may be brought into the active area 124 to imprint the magnetic signature 160 thereon.

The device 120 includes one or more magnets 132 and a magnet moving system 130. The magnet moving system 130 is configured to move the magnets 132, individually or as groups, toward and away from the active area 124. The one or more magnets 132 may be passive magnets configured to generate the one or more magnetic fields 135.

The device 120 may include a device engagement member 123 configured to receive at least the signature portion 115 of the medical device 110 and define the location of the signature portion 115 within the active area 124. In some embodiments, the device engagement member 123 may include a cavity 125, such as a trough, for example, configured to receive the medical device 110 therein.

In some embodiments, the device engagement member 123 may be positionable with respect to the body 122 including the active area 124. In some embodiments, the active area 124 may define a longitudinal axis 124A. In some embodiments, the signature portion 115 may be disposed parallel with the longitudinal axis 124A when the signature portion 115 is disposed within the active area 124. The device engagement member 123 may be longitudinally positionable so as to adjust a longitudinal position of the signature portion 115 within the active area 125. More specifically, the device engagement member 123 may be longitudinally positionable so as to adjust a longitudinal position of the signature portion 115 with respect to the one or more magnetic fields 135.

In some embodiments, the device 120 may include one or more sensors 126 in communication with the console 140. The one or more sensors 126 in combination with the console 140 may generally be configured to identify (i.e., determine an identity) of the *medica* device 110. In some embodiments, the one or more sensors 126 be configured to detect one or more characteristics (e.g., physical characteristics) of the medical device 110, such as the size of the medical device 110, the shape of the medical device 110, or the location of the ferrous elements on the medical device 110, for example. In some embodiments, the one or more characteristics may include a length and/or a diameter of a cannula. In some embodiments, the system 100 may determine the identity of the medical device 110 and define the magnetic signature 160 (i.e., established a defined magnetic signature) to be imprinted on the medical device 110 based on the identity. In some embodiments, the one or more sensors 126 may include any sensor suitable for determining a physical characteristic of the medical device, such as an impedance sensor, an optical sensor, a capacitive sensor, a proximity sensor, or a magnetometer, for example. The one or more sensors 126 may be configured to provide data or electrical signals to the console 140.

In some embodiments, the one or more sensors 126 may include an RFID reader and the medical device 110 may include an RFID tag (not shown), where the data acquired from the RFID tag includes the identity of the medical device. In some embodiments, the one or more sensors 126 may include a barcode reader, and the medical device 110 may associated with a barcode (not shown) where the barcode data includes the identity.

In some embodiments, the one or more sensors 126 may include the one or more magnetometers, where the one or more magnetometers in combination with console 140 are configured to detect the magnetic signature 160, i.e., read or otherwise obtain the imprinted magnetic signature 160 on the medical device 110.

In some embodiments, the system 100 may include a display 174 in communication with the console 140. In some embodiments, the display 174 may include a user interface 170. In some embodiments, the user interface 170 may be configured to allow a user to input the one or more characteristics of the medical device 110 to the console 140. The logic of the console 140 may be configured to activate the magnet moving system 130 to change the location or the orientation of the one or more magnets 132 within the active area 124 to imprint the magnetic signature 160 onto the medical device 110.

FIG. 1B illustrates a side view of the medical device 110 having the magnetic signature 160 imprinted on the signature portion 115. The medical device 110 may include a needle, a stylet, a guidewire, an obturator, a probe, a tunneller, a stent, a port, a balloon device, a sheath, or any other medical device without limit. The magnetic signature 150 includes a number (1, 2, 3, 4, 5, 6, or more) of magnetic dipoles 162 disposed along the signature portion 115. Each dipole 162 defines an orientation 163 in accordance with the North and South poles of the dipole 162. As such, the orientation of each dipole 162 may be a first orientation 163A or a second orientation 163B, where the second orientation 163B is rotated 180 degrees from the first orientation 162A. Each dipole 162 may also define a length 166. In some embodiments, the length 166 may be chosen from a number (e.g., 1, 2, 3, 4, 5, 6, or more) of discrete lengths. For example, a first dipole 132 may define a first length and a second dipole may define a second length, where the second length is different from the first length. Similarly, the magnetic signature 150 may include a spacing 164 between adjacent dipoles 132. In some embodiments, the spacing 164 may be chosen from a number (e.g., 1, 2, 3, 4, 5, 6, or more) of discrete spacings. For example, a first pair of adjacent dipoles 132 may define a first spacing and a second pair of adjacent dipoles 132 may define a second spacing, where the second spacing is different from the first spacing. In some embodiments, the dipoles 162 may include magnetized discreet ferrous elements 116. The magnetic signature 160 may include any combination of all or any subset of the number of dipoles 162, the spacing 164 between adjacent dipoles 162, the orientation 163 of each of the dipoles 162, and the length 166 of each of the dipoles 162. In some embodiments, the magnetic signature may include one or more magnetic multipoles.

FIG. 2 illustrates a side cross-sectional perspective view of the device 120, in accordance with some embodiments. The medical device 110 may be introduced into the active area 124 to be imprinted with the magnetic signature 160. In some embodiments, the signature portion 115 or the entire medical device 110 may be inserted into the active area 124.

The magnet moving system 130 may include one or more actuators 134 coupled to the one or more magnets 132. In some embodiments, each magnet 132 may include a corresponding actuator 134 operatively coupled therewith, such as via a shaft 136, for example. The actuator 134 may be activated to (i) displace the magnet 132 into an imprinting position 134A within the active area 124 and (ii) extract the magnet 132 away from the imprinting position 134. In some embodiments, the actuator 134 may linearly displace the magnet laterally toward the active area 124 in a direction perpendicular to the longitudinal axis 124A.

In some embodiments, all or a subset of one or more actuators 134 may include a rotating actuator 137 configured to change the orientation of the one or more magnets 132, i.e., rotate the magnet 180 degrees. Each magnet 132 includes an orientation of the North pole/South pole of the magnet 132 in relation to the longitudinal axis 124A. For example, the arrow 133A indicates a first orientation of the magnet 132 and the arrow 133B indicates a second orientation rotated 180 degrees from the first orientation. In some embodiments, the one or more actuators 134 may include one or more buttons. Each magnet 132 may independently change the position or orientation with respect to the active area 124 to change the magnetic signature 160. In some embodiments, the console 140 may define the movement of each of the magnets 132 to achieve a desired configuration of the magnets 132 for the magnetic signature 160. In some embodiments, each actuator 134 may be manually activated or may be automatically activated via logic of the console 140.

Each of the magnets 132 define a magnet length along the dipole direction (i.e., North to South). For example, a first magnet 132 may define a first magnet length and a second define a second magnet length that different from the first magnet length. In some embodiments, the magnet length may define the length 166 of a dipole 162 imprinted by the respective magnet 132.

The device 120 may include an engagement member actuator 123A operatively coupled between the device engagement member 123 and the body 122 via a suitable mechanism, such as a belt, a rack and pinion gears, or a power screw, for example. The engagement member actuator 123A may be configured to longitudinally displace the device engagement member 123 along or parallel to the longitudinal axis 124A. The engagement member actuator 123A may be coupled with the console 140 so that logic of the console 140 may displace the signature portion 115 relative to the one or magnetic fields in accordance with the magnetic signature 160. By way of one example of imprinting the magnetic signature 160, the logic may displace a defined magnet into and away from the signature portion 115 to imprint a first dipole 162 onto the signature portion 115 at a first location on the signature portion 115. Thereafter, the logic may adjust the position of the device engagement member 123 having the medical device 110 coupled therewith. The logic may the displace the defined magnet 132 into and away from the signature portion 115 to imprint a second dipole 162 onto the signature portion 115 at a second location on the signature portion 115.

FIG. 3 illustrates a block diagram of some components of the system 100, including the console 140, in accordance with some embodiments. In some embodiments, the console 140 may include the one or more processors 142, an energy source 144, the non-transitory computer-readable medium ("memory") 146 and the logic which may be composed of a plurality of logic modules. In some embodiments, the energy source 144 may include a rechargeable battery or an external power source. In some embodiments, the energy source 144 may power the one or more sensors 126. In some embodiments, the plurality of logic modules may include a sensor activation logic 148, a sensor receiving logic 150, a user input receiving logic 151, a magnetic signature determination logic 152, a magnet moving system activation logic 154, a magnetic signature imprinting logic 156, a magnetic signature verification logic 158, and a data store 159. In some embodiments, the sensor activation logic 148 may be configured to activate the one or more sensors 126 to determine the identity of the medical device 110. In some embodiments, the sensor receiving logic 150 may be configured to receive data and/or electrical signals from the one or more sensors 126. In some embodiments, the data and/or electrical signals may correspond to the one or more characteristics of the medical device 110 as described above. In some embodiments, the user input receiving logic 151 may be configured to receive input from the user interface 170, such as input pertaining to the identity or the one or more characteristics of the medical device 110, for example.

In some embodiments, the magnetic signature determination logic 152 may be configured to determine the identity of the medical device 110 and define the magnetic signature 160 to be imprinted thereon, based on the identity. In some embodiments, the magnet moving system activation logic 154 may activate the actuators 134 to move all or any subset of the one or more of the magnets 132 into and away from of the imprinting position 134A to imprint the magnetic signature 160 onto the signature portion 115. In some embodiments, the magnet moving system activation logic 154 may be configured to activate any subset of the rotating actuators 137 change the orientation of a corresponding subset of the one or more magnets 132. In some embodiments, the magnetic signature imprinting logic 156 may be configured to activate the engagement member actuator 123A to move the medical device 110 adjust the position of the signature portion 115 within the active area 124 to imprint the magnetic signature thereon.

In some embodiments, the magnetic signature verification logic 158 may be configured to verify the magnetic signature 160 imprinted on the medical device 110 is the same as the defined magnetic signature 160 to be imprinted on the medical device 110. In some embodiments, the magnetic signature verification logic 158 may compare the magnetic signature 160 imprinted with the defined magnetic signature 160. In some embodiments, the magnetic signature verification logic 158 may provide an alert to the operator in response to the comparison. In some embodiments, the magnetic signature verification logic 158 may receive data and/or electrical signals from the one or more magnetometers 126 to determine the magnetic signature 160 imprinted on the medical device 110. In some embodiments, the data store 159 may be configured to store templates of the multiple magnetic signatures imprinted corresponding to multiple medical devices. In some embodiments, the console 140 may be in communication with a computing device or an electronic medical record system.

FIG. 4 is a perspective view of the device 120 illustrating an exemplary method of imprinting the magnetic signature 160 onto the medical device 110, in accordance with some embodiments. The signature portion 115 of the medical 110 is disposed within the cavity 125 of the device engagement member 123. The device engagement member 123 is configured to move through or along the active area 124, thereby moving the signature portion 115 over the one or more magnets 132 to imprint the magnetic signature thereon. As the medical device 110 longitudinally moved through the active area 124, the magnet moving system 130 may displace the one or more of the magnets 132 into the imprinting position 134A and extract the one or more of the magnets 132 away from the imprinting position 134A. The logic of the console may automatically move the signature portion 115 through the active area 124 by activating the engagement member actuator 123A while displacing and extracting the one or more magnets 132 into and away from the imprinting position 134A. In some embodiments, the method may include changing the orientation of any one of the one or more magnets 132. Changing the location and the orientation of the one or more magnets 132 within the active area 124 along with the movement of the medical device 110 along the device bed 125C imprints the magnetic signature 160 onto the medical device 110.

FIG. 5 illustrates a flow chart of an exemplary method 500 of imprinting a magnetic signature onto the medical device 110 that, in accordance with some embodiments, includes all or a subset of the following steps or processes.

The method includes receiving the medical device within the active area (block 502). In some embodiments, embodiments receiving the medical device includes receiving the medical device from an operator into a trough of the device engagement member. In some embodiments, embodiments receiving the medical device includes receiving the medical device into the imprinting space.

In some embodiments, the method 500 includes determining an identity of the medical device (block 504). Determining the identity may include determining the type of medical device, such as a needle, a stylet, a guidewire, an obturator, a probe, or a tunneller. In some embodiments, determining an identity of the medical device includes detecting and identifying one or more characteristics of the medical device including physical characteristics, such as the size of the medical device, the shape of the medical device, the location of the ferrous elements on the medical device, for example. In some embodiments, determining an identity of the medical device includes obtaining receiving RFID data from a RFID tag associated with the medical device, where the RFID data includes the identity. In some embodiments, determining an identity of the medical device includes obtaining receiving barcode data from a barcode associated with the medical device, where the barcode data includes the identity.

In some embodiments, the method 500 includes defining the magnetic signature to imprint onto the medical device 110 (block 506) or in other words, determining a defined magnetic signature to imprint onto the medical device 110 (block 506). In some embodiments, the determining the defined magnetic signature to imprint onto the medical device includes determining the magnetic signature based on the determined identity. In some embodiments, determining the defined magnetic signature to imprint onto the medical device includes choosing a magnetic signature from a plurality a magnetic signatures stored in memory where each of the plurality a magnetic signatures is linked to an identity of one of a corresponding plurality of medical devices.

In some embodiments, the method 500 further includes imprinting a magnetic signature onto the medical device (block 508) or in other words, defining an imprinted magnetic signature on the medical device. In some embodiments, imprinting a magnetic signature includes imprinting the defined magnetic onto the medical device. In some embodiments, imprinting the magnetic signature includes displacing a subset of a number of magnets of the system into the imprinting position, where the subset of a number of magnets is chosen based on the defined magnetic signature. In some embodiments of the method, imprinting the magnetic signature includes activating the orienting actuators coupled with subset of the number of magnets to rotate the magnets of the subset of the number of magnets from a first magnet orientation to a second magnet orientation based on the defined magnetic signature. In some embodiments of the method, imprinting the magnetic signature includes imprinting a set of dipoles onto the medical device having one length and imprinting another set of dipoles onto the medical device having a different length the method. In some embodiments of the method, imprinting the magnetic signature includes (i) imprinting a first pair of dipoles having a first spacing between the dipoles of the first pair and (ii) imprinting a second pair of dipoles having a second spacing between the dipoles of the second pair, where second spacing is different from the first spacing.

In some embodiments, the method 500 further includes validating that the imprinted magnetic signature matches the defined magnetic signature validating the magnetic signature of the medical device (block 510). In some embodiments of the method, validating the imprinted magnetic signature includes (i) determining the imprinted magnetic signature via the number of magnetometers of the system and (ii) comparing the imprinted magnetic signature with the defined magnetic signature to verify that the imprinted magnetic signature matches the defined magnetic signature.

FIG. 6 is a top view of another embodiment of an imprinting device 620 that can, in certain respects, resemble components of the imprinting device 120 described in connection with FIGS. 1A-3. It will be appreciated that all the illustrated embodiments may have analogous features. Accordingly, like features are designated with like reference numerals, with the leading digits of "6." For instance, the body is designated as "122" in FIGS. 1A-3, and an analogous body is designated as "622" in FIG. 6. Relevant disclosure set forth above regarding similarly identified features thus may not be repeated hereafter. Moreover, specific features of the imprinting device 120 and related components shown in FIGS. 1A-3 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the imprinting device 620 of FIG. 6. Any suitable combination of the features, and variations of the same, described with respect to the imprinting device 120 and components illustrated in FIGS. 1A-3 can be employed with the imprinting device 620 and components of FIG. 6, and vice versa. This pattern of disclosure applies equally to further embodiments depicted in subsequent figures and described hereafter.

The imprinting device 620 is includes a turntable 638 having the one or more magnets 632 coupled thereon that may define a functionality that in some respects resembles the functionality of the linear array of magnets of the imprinting device 620. In some embodiments, the imprinting device 620 includes the active area 624 having the cavity 625 therein. The turntable 638 rotates about turntable axis 639 (shown perpendicular to the page), where the turntable axis 639 is oriented perpendicular to the longitudinal axis 624A of the active area 624. A magnet moving system 630 includes the turntable 638 operatively coupled with a turntable actuator 634 (shown hidden under the turntable 638), where the turntable actuator 634 is configured to rotate the turntable 638. The turntable actuator 634 is coupled with the console 640, so that logic of the console 640 may rotate the turntable 638 in accordance with imprinting the defined magnetic signature onto the medical device 120.

During use, as the medical device 110 is displaced along the active area 624 via the engagement member 623, the turntable 138 may rotate to move a subset of the one or more magnets 632 into and away from the imprinting position to imprint the magnetic signature. The one or more magnets 632 may include magnets having different orientations so that the diploes of the imprinted magnetic signature may have different orientations.

FIG. 7 illustrates a top cross sectional view of another embodiment of an imprinting device 720 In some embodiments, the imprinting device 720 includes the active area 724 disposed along the engagement member 723. In some embodiments, the magnet moving system 730 includes a number (e.g., 1, 2, 3, 4 or more) wheels, such as the two wheels 738A, 738B, for example. The wheels 738A, 738B are disposed adjacent the active area 724 so that the magnets 732, attached to or incorporated into the wheels 738A, 738B, may move into and out of the active area 724 via rotation of the wheels 738A, 738B. The wheels 738A, 738B rotate about corresponding wheel axes 739A, 739B. In some embodiments, the wheel axes 739A, 739B may be disposed parallel to the longitudinal axis 724A. In some embodiments, the wheels 738A, 738B are disposed on opposite sides of the active area 724. In other embodiments, the first wheel 738A may be adjacent the second wheel 738B, or in other words, the two wheels 738A, 738B may be disposed at a common longitudinal position along the active area 724. In other embodiments, the two wheels 738A, 738B or may be disposed at different longitudinal positions along the active area 724. In some embodiments, the one or more magnets 732 may be disposed in the same orientation or in different orientations. In some embodiments, a first magnet 732 the first wheel 738A may be disposed in the same orientation as a second magnet 732 the second wheel 738B, and during operation, the first magnet and the second magnet are simultaneously disposed adjacent the medical device 110 to imprint the magnetic signature. The wheels 738A, 738B are sized and positioned so that rotation of the wheels 738A, 738B displaces the magnets 732 into and away from the imprinting position. The one or more magnetic fields (not shown) generated by one or more magnets 732 are configured to imprint the magnetic signature onto the medical device 110 when the one or more magnets 732 are disposed in the imprinting position. During operation, the rotation of the wheels 738A, 738B may be combined with the movement of the medical device 110 via the device engagement member 723 to imprint the defined magnetic signature onto the medical device 110.

The wheels 738A, 738B are operatively coupled with wheel actuators 734A, 734B, respectively, and the wheel actuators 734A, 734B are coupled with the console 740 so that logic of the console 740 may rotate the wheels 738A, 738B to imprint a defined magnetic signature onto the medical device 110. In some embodiments, the one or more wheels 738 may be configured (e.g., oriented, sized and positioned) to pull and/or push the medical device 710 through the active area 724.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A magnetic signature imprinting system, comprising:
   an imprinting apparatus configured to operatively engage a medical device, the imprinting apparatus, comprising:
      a frame;
      a device engagement member coupled with the frame, the device engagement member configured to receive and position a signature portion of the medical device within an imprinting space of the frame; and
      a number of magnets selectively positionable with respect to the imprinting space via one or more magnet actuators coupled between the number of magnets and the frame; and
   a console coupled with the one or more magnet actuators, the console having a number of processors and a non-transitory computer-readable medium having logic stored thereon that, when executed by the number of processors, performs operations that include activating the one or more magnet actuators to (i) displace the number of magnets into an imprinting position defining a magnetic field within the imprinting space, the magnetic field configured to imprint a defined magnetic signature on the signature portion to define an imprinted magnetic signature and (ii) displace the number of magnets away from the imprinting position.

2. The system according to claim 1, wherein the medical device includes a needle, a stylet, a guidewire, an obturator, a probe, or a tunneller.

3. The system according to claim 1, wherein the magnetic signature includes one or more multipoles disposed along the signature portion.

4. The system according to claim 1, wherein the device engagement member includes a trough configured to receive the signature portion of the medical device therein.

5. The system according to claim 1, further comprising a number of magnetometers coupled with the console, the number of magnetometers configured to detect the magnetic field generated by the imprinted magnetic signature on the medical device,
   wherein the operations further include:
      receiving electrical signals from the number of magnetometers based on the magnetic field generated by the imprinted magnetic signature;
      determining the imprinted magnetic signature on the medical device based on the electrical signals from the number of magnetometers;
      comparing the imprinted magnetic signature with the defined magnetic signature to verify that the imprinted magnetic signature matches the defined magnetic signature; and
      providing an alert to an operator in response to the comparing.

6. The system according to claim 1, wherein activating the one or more magnet actuators includes selectively (i) displacing at least a first subset of the number of magnets into the imprinting position and (ii) extracting the at least first subset of the number of magnets away from the imprinting position, the at least first subset of the number of magnets chosen based on the defined magnetic signature.

7. The system according to claim 1, wherein the number of magnets includes at least a second subset having a second magnet length and at least a third subset having a third magnet length that is different from the second magnet length.

8. The system according to claim 1, wherein the imprinted magnetic signature includes a series of dipoles disposed along the signature portion.

9. The system according to claim 8, wherein at least one dipole includes a first length and at least one other dipole includes a second length different from the first length.

10. The system according to claim 8, wherein at least one dipole includes a first orientation and at least one other dipole includes a second orientation rotated 180 degrees from the first orientation.

11. The system according to claim 8, wherein a first spacing between a first pair of adjacent dipoles is different from a second spacing between a second pair of adjacent dipoles.

12. The system according to claim 1, wherein the number of magnets includes passive magnets.

13. The system according to claim 12, wherein the passive magnets include multipoles.

14. The system according to claim 1, further comprising:
a number of identification sensors coupled with the console, the number of identification sensors configured to provide at least one of data or electrical signals associated with one or more characteristics of the medical device,
wherein the operations further include:
receiving the at least one of data or electrical signals from the number of identification sensors;
determining an identity of the medical device based on the at least one of data or electrical signals; and
establishing the defined magnetic signature based on the identity.

15. The system according to claim 10, wherein:
the number of identification sensors includes a radio frequency identification (RFID) reader, and
the operations further include receiving RFID data from an RFID tag associated with the medical device, the RFID data including the identity.

16. The system according to claim 14, wherein:
the number of identification sensors includes a barcode reader, and
the operations further include obtaining barcode data from a barcode associated with the medical device, the barcode data including the identity.

17. The system according to claim 14, wherein:
the number of identification sensors include one or more first sensors configured to provide the at least one of data or electrical signals based on a number of physical characteristics of the medical device, and
the operations further include determining the identity based on the number of physical characteristics.

18. The system according to claim 17, wherein the one or more first sensors include at least one of an inductive sensor, an impedance sensor, a capacitive sensor, or an optical sensor.

19. The system according to claim 17, wherein the number of physical characteristics include one or more of a physical dimension or a shape of the medical device.

20. The system according to claim 19, wherein the physical dimension includes at least one of a length or a diameter of a cannula.

21. The system according to claim 1, wherein at least a fourth subset of the number of magnets is rotatable between a first magnet orientation and a second magnet orientation rotated 180 degrees with respect to the first magnet orientation.

22. The system according to claim 21, wherein:
the imprinting apparatus includes one or more orienting actuators coupled between
the at least fourth subset of the number of magnets and the frame, and
the operations further include activating the one or more orienting actuators to selectively rotate one or more of the at least fourth subset of the number of magnets between the first magnet orientation and the second magnet orientation based on the defined magnetic signature.

23. The system according to claim 1, wherein:
at least a fifth subset of the number of magnets includes magnets arranged in linear array extending along a longitudinal axis of the imprinting space,
each of the at least fifth subset of the number of magnets is coupled to the frame via a linear magnet actuator, and
activating the one or more magnet actuators includes activating one or more of the linear magnet actuators to linearly displace one or more of the at least fifth subset of the number of magnets laterally toward the longitudinal axis of the imprinting space based on the defined magnetic signature.

24. The system according to claim 23, wherein:
at least a sixth subset of the number of magnets includes magnets arranged along a turntable,
the turntable is rotatable about a turntable axis that is oriented perpendicular to the longitudinal axis of the imprinting space so that rotating the turntable selectively displaces each of magnets of the at least sixth subset into and away from the imprinting position,
the turntable is coupled with the frame via a turntable actuator, and
activating the one or more magnet actuators includes activating the turntable actuator based on the defined magnetic signature.

25. The system according to claim 24, wherein:
at least a seventh subset of the number of magnets includes magnets arranged along a circumference of a number of wheels,
each of the number of wheels is rotatable about a corresponding wheel axis that is oriented parallel to the longitudinal axis of the imprinting space so that rotating the number of wheels displaces each of the magnets of the seventh subset into and away from the imprinting position,
each wheel is coupled with the frame via a corresponding wheel actuator, and
activating the one or more magnet actuators includes selectively activating at least one of the corresponding wheel actuators based on the defined magnetic signature.

26. The system according to claim 25, wherein the magnets of the at least fifth, sixth, and seventh subsets include dipoles having different dipole lengths and different dipole orientations.

27. The system according to claim 1, wherein:
the device engagement member is coupled with the frame via an engagement member actuator configured to displace the engagement member along a longitudinal axis of the imprinting space,
the operations further include activating the engagement member actuator based on the defined magnetic signature to displace the engagement member between (i) a first engagement member position defining a first longitudinal position of the signature portion within the imprinting space and (ii) at least a second engagement member position defining a second longitudinal position of the signature portion within the imprinting space, and the first engagement member position is different from the at least second engagement member position.

28. The system according to claim 27, wherein:

the imprinting apparatus includes a number of position sensors configured to determine a longitudinal position of the signature portion within the imprinting space, and the operations further include at least one of notifying an operator regarding the longitudinal position of the signature portion or activating the engagement member actuator to adjust the longitudinal position of the signature portion.

29. The system according to claim 28, wherein:

the number of position sensors include one or more magnetometers configured to determine the longitudinal position of at least a portion of the imprinted magnetic signature within the imprinting space, and the operations further include activating the engagement member actuator to adjust the longitudinal position of the at least a portion of the imprinted magnetic signature within the imprinting space.

\* \* \* \* \*